United States Patent
Phan

(10) Patent No.: US 6,544,237 B1
(45) Date of Patent: Apr. 8, 2003

(54) HAND-PUMPED ENEMA APPARATUS AND METHOD

(76) Inventor: Han Ngoc Phan, 10407 New Hampshire Ave., Silver Spring, MD (US) 20903

(*) Notice: Subject to any disclaimer, the term of this patent is extended or adjusted under 35 U.S.C. 154(b) by 0 days.

(21) Appl. No.: 10/023,823

(22) Filed: Dec. 21, 2001

Related U.S. Application Data

(60) Provisional application No. 60/277,655, filed on Mar. 22, 2001.

(51) Int. Cl.$^7$ .......................... A61M 5/00; A61M 31/00
(52) U.S. Cl. ..................... 604/257; 604/187; 604/279
(58) Field of Search ........................ 604/27–29, 36, 604/276, 34–38, 113, 73, 212, 149, 279, 359, 30, 500, 122, 278, 322, 299, 216, 262, 32, 408, 911, 98.02, 523, 105, 403, 131, 142, 80, 247, 132, 153, 916, 118

(56) References Cited

U.S. PATENT DOCUMENTS

| | | |
|---|---|---|
| 331,128 A | 11/1885 | Gordon et al. |
| 493,208 A | 3/1893 | Cruickshank |
| 1,493,592 A | 5/1924 | Beck |
| 1,494,985 A | 5/1924 | Beck |
| 1,847,954 A | 3/1932 | Fisher |
| 1,925,230 A | 9/1933 | Buckhout |
| 3,398,743 A | 8/1968 | Shalit |
| 3,724,461 A | * 4/1973 | Eisenberg .................. 604/262 |
| 3,889,676 A | * 6/1975 | Greene .................. 604/101.05 |
| 4,248,226 A | * 2/1981 | Pitchford, Jr. ............. 604/246 |
| 4,525,156 A | * 6/1985 | Benusa et al. ................ 604/28 |
| 5,009,635 A | 4/1991 | Scarberry |
| 5,356,375 A | * 10/1994 | Higley ......................... 604/30 |
| 5,405,319 A | * 4/1995 | Abell et al. .................. 604/27 |

FOREIGN PATENT DOCUMENTS

| | | |
|---|---|---|
| CH | 688 847 | 4/1998 |
| DE | 102135 | 7/1898 |

* cited by examiner

Primary Examiner—Michael J. Hayes
Assistant Examiner—Roz Ghafoorian
(74) Attorney, Agent, or Firm—Stephen Christopher Swift; Swift Law Office

(57) ABSTRACT

An enema apparatus, including a container for liquid, an inlet situated within the container, a first conduit connected to the inlet and passing outside the container, a hand pump connected to the first conduit, a second conduit connected to the hand pump and passing inside the container, an outlet connected to the second conduit, the outlet being situated in and passing through a side of the container, and a third conduit, having a first end connected to the outlet, and a second end connected to a syringe. When a user activates the hand pump, liquid passes from the container, through the inlet to the first conduit, through the first conduit to the hand pump, through the hand pump to the second conduit, through the second conduit to the outlet, through the outlet to the third conduit, through the third conduit to the syringe, and out the syringe.

19 Claims, 2 Drawing Sheets

HAND-PUMPED ENEMA APPARATUS AND METHOD

CROSS REFERENCE TO RELATED APPLICATION

This application is based on Provisional Patent Application Serial No. 60/277,655, filed Mar. 22, 2001.

BACKGROUND OF THE INVENTION

1. Field of the Invention

The present invention relates to enema devices, specifically, enema devices that are hand-pumped.

2. Description of the Prior Art

U.S. Pat. No. 331,128, issued on Nov. 24, 1885, to John Wesley Gordon and George Turner Blanchard, discloses a vaginal irrigator, having a cylindrical container with an open top, an intake submerged in liquid in the container and connected to a tube connected to a hand pump connected to another tube connected to a syringe. The present invention is distinguishable, in that the intake and tubing are attached to and pass through the sides of the container, thus reducing the chance of liquid being spilled.

U.S. Pat. No. 493,208, issued on Mar. 7, 1893, to Arthur B. Cruikshank, discloses a vaginal syringe, with a hand pump divided into two compartments, that pumps liquid both into and out of the vagina.

U.S. Pat. No. 1,493,592, issued on May 13, 1924, to Friedrich C. Beck, discloses a syringe for hygienic purposes, with a hand pump that pumps liquid out of a closed container, and a second tube by which the liquid is returned to the same container.

U.S. Pat. No. 1,494,985, issued on May 20, 1924, again to Friedrich Conrad Beck, discloses another syringe for hygienic purposes, in which the liquid is returned to a different compartment in the container.

U.S. Pat. No. 1,847,954, issued on Mar. 1, 1932, to Arthur R. Fisher, discloses a colon irrigator, in which a compressible bulb hand pump is used to remove liquid from the bottom of a jar into a syringe. The jar is supported on a stand. The present invention is distinguishable, in that its container can rest on the floor or other flat surface by itself, and liquid is removed through the side rather than the bottom of the container.

U.S. Pat. No. 1,925,230, issued on Sep. 5, 1933, to Halsey L. Buckhout, discloses a syringe with a cylindrical container have a top cover by which it can be closed. Liquid can be removed from the container by a tube that passed through the cover and is connected to a compressible bulb hand pump, which is connected by another tube to the syringe. The present invention is distinguishable in that the container does not have a cover, and liquid is removed from the side of the container.

U.S. Pat. No. 3,398,743, issued on Aug. 27, 1968, to Shimon Shalit, discloses a closed system irrigating apparatus for viscous organs, having a compressible bulb with two compartments, by which liquid is simultaneously pumped in opposite directions both in and out of the organ being irrigated.

U.S. Pat. No. 5,009,635, issued on Apr. 23, 1991, to Eugene N. Scarberry, discloses a pump apparatus, which is designed to pump liquid into a container, rather than out of it as in the present invention.

U.S. Pat. No. 5,405,319, issued on Apr. 11, 1995, to Roy Abell and Thomas Shilling, discloses a bowel evacuation system, in which liquid flows out of a water bag under the force of gravity alone. Squeeze bulbs are used to open checks valves, and to inflate a cuff, but not for pumping water.

German Patent No. 102135, issued on Jul. 2, 1898, to Ignaz Schille, discloses an irrigation apparatus in which liquid is removed from a first compartment of a container by a compressible bulb hand pump, and then passes in a tube through a second compartment of the container into and out of a syringe. The liquid then returns to the second compartment.

Swiss Patent No. 688 847, issued on Apr. 30, 1998, to Anton Grassmann, discloses an apparatus having a bulb attached to tubing. At the opposite end of the tubing, a syringe is removably attached. There is no container from which liquid can be continuously pumped, as in the present invention.

None of the above inventions and patents, taken either singly or in combination, is seen to describe the instant invention as claimed.

SUMMARY OF THE INVENTION

The present invention is an enema apparatus, including a container for liquid, an inlet situated within the container, a first conduit connected to the inlet and passing outside the container, a hand pump connected to the first conduit, a second conduit connected to the hand pump and passing inside the container, an outlet connected to the second conduit, the outlet being situated in and passing through a side of the container, and a third conduit, having a first end connected to the outlet, and a second end connected to a syringe. When a user activates the hand pump, liquid passes from the container, through the inlet to the first conduit, through the first conduit to the hand pump, through the hand pump to the second conduit, through the second conduit to the outlet, through the outlet to the third conduit, through the third conduit to the syringe, and out the syringe. In the preferred embodiment, the hand pump is a resilient flexible bulb, with at least one check valve, and is activated by repeated squeezing of the bulb. The first, second and third conduits are preferably made of flexible plastic tubing; the inlet and outlet are preferably made of metal. The container is preferably a plastic bowl with an open top.

Accordingly, it is a principal object of the invention to provide a new and improved enema apparatus.

It is another object of the invention to provide an enema apparatus under which water or other liquid may be pumped into a bodily orifice.

It is a further object of the invention to provide an enema apparatus into which water or other liquid can be easily poured through an open top.

Still another object of the invention is to provide and enema apparatus that is inexpensive and can be used at home.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
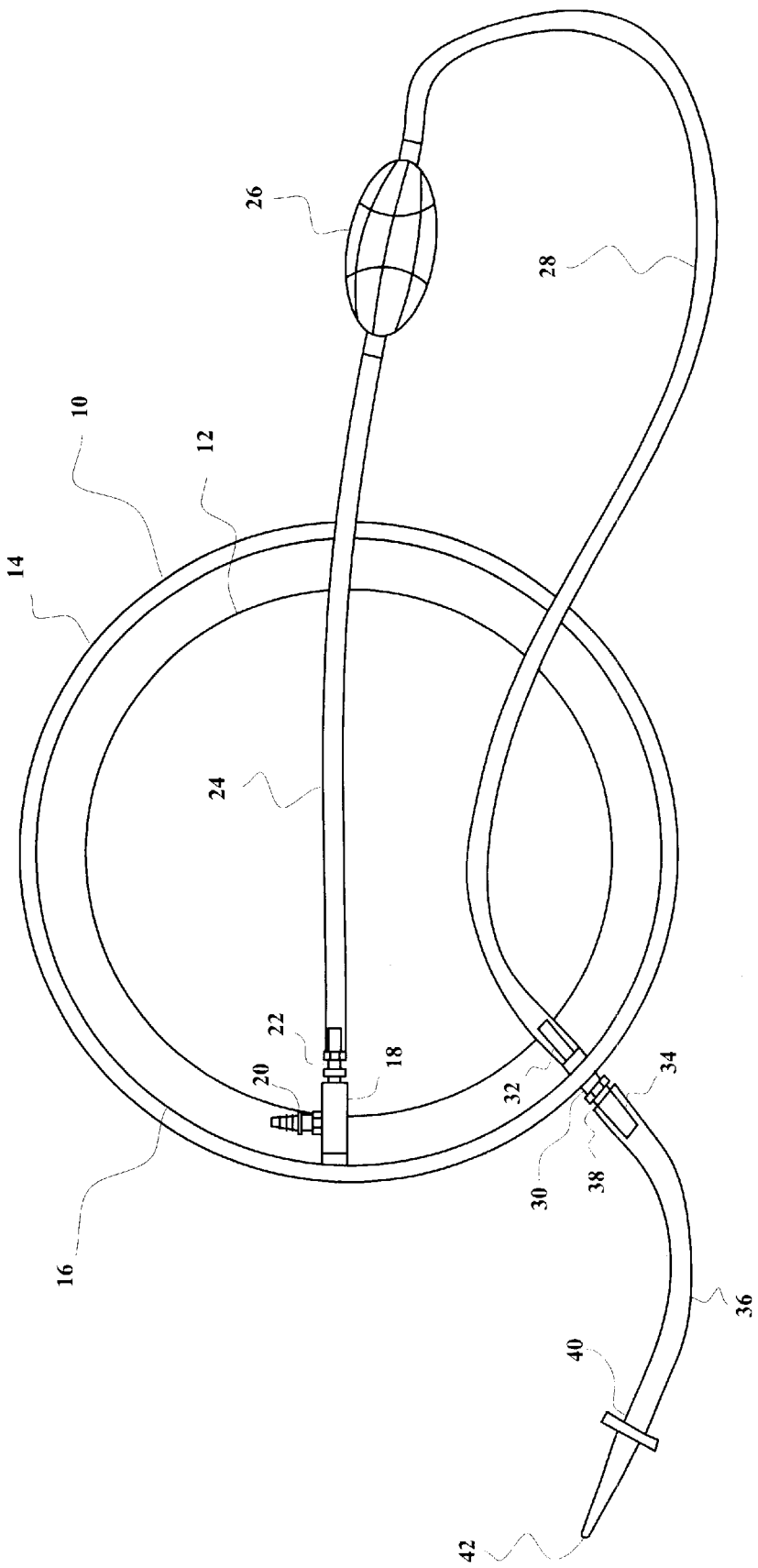
FIG. 1 is a top plan view of the preferred embodiment of the invention.
Figure 2:
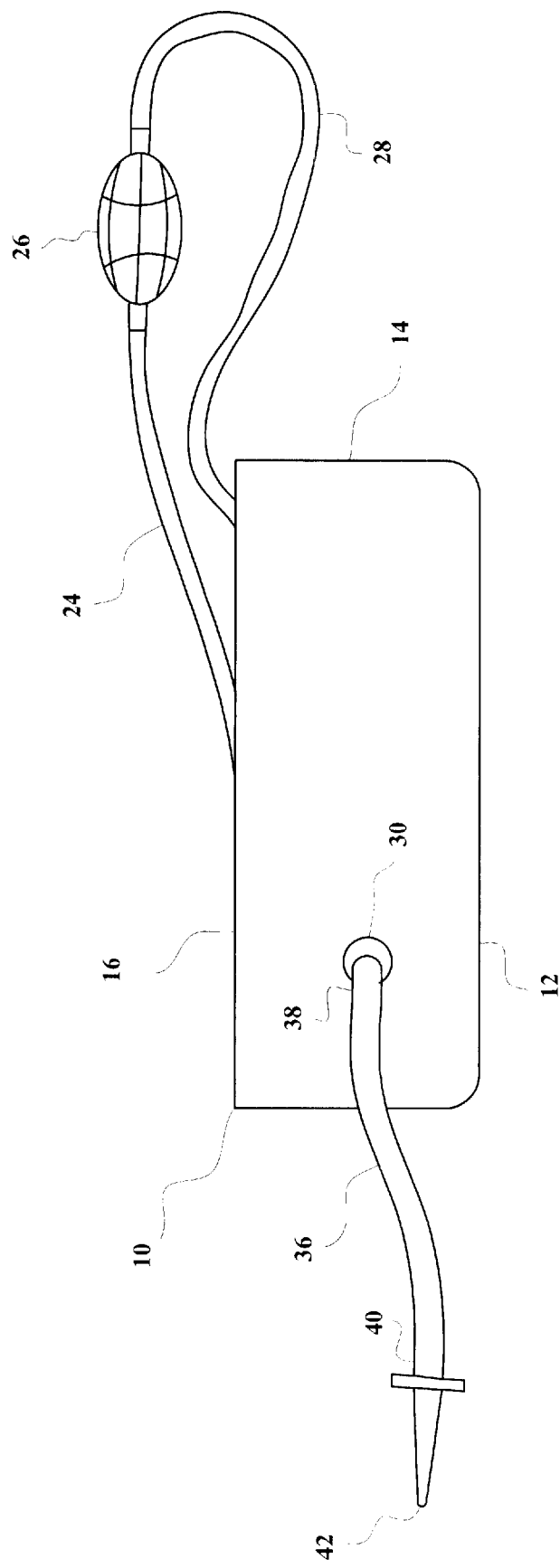
FIG. 2 is a side elevational view of the preferred embodiment of the invention.

The present invention is an enema apparatus, the preferred embodiment of which is shown in a top plan view in FIG. 1, and in a side elevational view in FIG. 2. It includes a container 10 for water or other liquid, which is preferably a generally cylindrical plastic bowl with a flat bottom 12, a single circular side 14, and an open top 16. The inlet 18 is situated within the container and attached to its side. The inlet has a first nozzzle 20 into which liquid in the container flows and a second nozzle 22. The first conduit 24 is connected to the second nozzle of the inlet and passes outside the container. The hand pump 26 is connected to the first conduit. The second conduit 28 is connected to the hand pump and passes back inside the container. The outlet 30 has a first nozzle 32 within the container that is connected to the second conduit, and a second nozzle 34 outside the container. The outlet is situated in and passes through the side of the container. The third conduit 36, has a first end 38 connected to the second nozzle of the outlet, and a second end 40 connected to the syringe 42.

When a user activates the hand pump, liquid passes from the container, through the inlet to the first conduit, through the first conduit to the hand pump, through the hand pump to the second conduit, through the second conduit to the outlet, through the outlet to the third conduit, through the third conduit to the syringe, and out the syringe. In the preferred embodiment, the hand pump is a resilient flexible bulb, made of plastic, rubber or other suitable material, with at least one check valve, and is activated by repeated squeezing of the bulb. The first, second and third conduits are preferably made of flexible plastic tubing. Alternatively, the conduits may be made of rubber or other material suitable for flexible tubing. The inlet and outlet are preferably made of copper or other metal. The syringe may be made of plastic, rubber, or other suitable material, and is designed to be inserted into a bodily orifice such as the anus or vagina.

In the preferred embodiment, there is a ball (not shown in the drawings) contained inside the inlet 18. When the hand pump is squeezed, the pressure causes the ball to be pushed into the entrance to the first nozzle 20, thus preventing the liquid from flowing back out through the inlet. When the hand pump is released, the ball floats away from the entrance to the first nozzle, thus allowing more liquid to flow through the inlet. Alternatively, a check valve may be used to prevent reverse flow of liquid through the inlet.

It is to be understood that the present invention is not limited to the sole embodiment described above, but encompasses any and all embodiments within the scope of the following claims.

I claim:

1. An enema apparatus, comprising:

a container for liquid;

an inlet situated within the container;

a first conduit connected to the inlet and passing outside the container;

a hand pump connected to the first conduit;

a second conduit connected to the hand pump and passing inside the container;

an outlet connected to the second conduit, the outlet being situated in and passing through a side of the container; and a third conduit, having a first end connected to the outlet, and a second end connected to a syringe;

whereby, when a user activates the hand pump, liquid passes from the container, through the inlet to the first conduit, through the first conduit to the hand pump, through the hand pump to the second conduit, through the second conduit to the outlet, through the outlet to the third conduit, through the third conduit to the syringe, and out the syringe.

2. The enema apparatus according to claim 1, wherein the hand pump comprises a resilient flexible bulb, with at least one check valve, and is activated by repeated squeezing of the bulb.

3. The enema apparatus according to claim 2, wherein first, second and third conduits are made of flexible tubing.

4. The enema apparatus according to claim 3, wherein the inlet and outlet are made of metal.

5. The enema apparatus according to claim 4, wherein the container is a bowl with an open top.

6. The enema apparatus according to claim 5, wherein the bowl is generally cylindrical, and has a flat bottom and a single cylindrical side.

7. The enema apparatus according to claim 6, wherein the inlet is attached to the side of the bowl.

8. The enema apparatus according to claim 7, wherein the bowl is made of plastic.

9. The enema apparatus according to claim 7, wherein the hand pump is made of plastic.

10. The enema apparatus according to claim 7, wherein the hand pump is made of rubber.

11. The enema apparatus according to claim 7, wherein the first, second and third conduits are made of plastic.

12. The enema apparatus according to claim 7, wherein the first, second and third conduits are made of rubber.

13. The enema apparatus according to claim 7, wherein the inlet is made of copper.

14. The enema apparatus according to claim 7, wherein the outlet is made of copper.

15. The enema apparatus according to claim 7, wherein the syringe is made of plastic.

16. The enema apparatus according to claim 7, wherein the syringe is made of rubber.

17. The enema apparatus according to claim 7, wherein the inlet has a first nozzle through which liquid in the bowl can enter, and a second nozzle connected to the first conduit, through which the liquid can flow into the first conduit to the hand pump.

18. The enema apparatus according to claim 17, wherein there is a ball contained inside the inlet, whereby when the hand pump is squeezed, resulting pressure causes the ball to be pushed into an entrance to the first nozzle, thus preventing the liquid from flowing back out through the inlet, and when the hand pump is released, the ball floats away from the entrance to the first nozzle, thus allowing more liquid to flow through the inlet.

19. The enema apparatus according to claim 17, wherein there is a check valve in the inlet.

* * * * *